(12) United States Patent
Dallman et al.

(10) Patent No.: US 7,238,723 B2
(45) Date of Patent: Jul. 3, 2007

(54) INDOLE DERIVATIVES

(75) Inventors: Christopher Ian Dallman, Sandwich (GB); Ronald James Ogilvie, Sandwich (GB)

(73) Assignee: Pfizer Inc., New York, NY (US)

( * ) Notice: Subject to any disclaimer, the term of this patent is extended or adjusted under 35 U.S.C. 154(b) by 282 days.

(21) Appl. No.: 10/376,385

(22) Filed: Feb. 27, 2003

(65) Prior Publication Data

US 2005/0131237 A1 Jun. 16, 2005

(51) Int. Cl.
*A61K 31/405* (2006.01)
*C07D 409/12* (2006.01)

(52) U.S. Cl. .................................. 514/415; 548/468
(58) Field of Classification Search ................ 548/468; 514/415
See application file for complete search history.

(56) References Cited

U.S. PATENT DOCUMENTS

| 3,952,741 | A |   | 4/1976  | Baker |
| 5,112,621 | A |   | 5/1992  | Stevens et al. |
| 5,464,633 | A |   | 11/1995 | Conte et al. |
| 5,474,784 | A |   | 12/1995 | Stevens et al. |
| 5,545,644 | A | * | 8/1996  | Macor et al. ............ 514/323 |
| 5,712,300 | A | * | 1/1998  | Jacobsen .................. 514/389 |
| 5,994,387 | A |   | 11/1999 | Wythes |
| 6,110,940 | A | * | 8/2000  | Harding et al. ........... 514/323 |

FOREIGN PATENT DOCUMENTS

| WO | WO 92/06973 | 4/1992 |
| WO | WO 96/06842 | 3/1996 |
| WO | WO 98/27089 | 6/1998 |
| WO | WO 98/39327 | 9/1998 |
| WO | WO 99/01135 | 1/1999 |

OTHER PUBLICATIONS

Jones et al., Pharmacology, Biochemistry and Behaviour 71, (2002) 555-568, Medical benefit of 5-HT-research.*
Robichaud et al., Annual Reports in Medicinal Chemistry, 200, 11-20, 35.*

* cited by examiner

*Primary Examiner*—James O. Wilson
*Assistant Examiner*—Ebenezer Sackey
(74) *Attorney, Agent, or Firm*—Charles W. Ashbrook; David R. Kurlandsky

(57) ABSTRACT

The present invention provides eletriptan hydrobromide monohydrate of the formula (I):

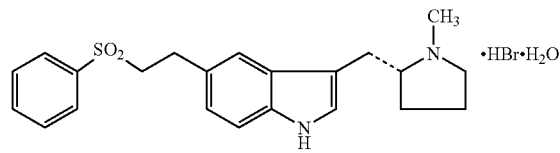

together with processes for preparing, uses of, and compositions containing, said monohydrate.

9 Claims, 7 Drawing Sheets

PXRD pattern of eletriptan hydrobromide monohydrate

DSC thermogram for eletriptan hydrobromide monohydrate

Moisture sorption isotherm for eletriptan hydrobromide monohydrate at 30°C.

FT-IR spectrum of eletriptan hydrobromide monohydrate (4000 – 400 cm⁻¹)

FT-IR spectrum of eletriptan hydrobromide monohydrate (1800 - 400 cm$^{-1}$)

DSC thermogram for Example 5

DSC thermogram for Example 6

INDOLE DERIVATIVES

This invention relates to indole derivatives. More specifically the present invention relates to eletriptan hydrobromide monohydrate, to processes for the preparation thereof, to processes for its conversion to anhydrous eletriptan hydrobromide, and to the uses of, and to compositions containing, said monohydrate.

Eletriptan, 3-([1-methylpyrrolidin-2(R)yl]methyl)-5-(2-phenylsulphonylethyl)-1H-indole, has the formula:

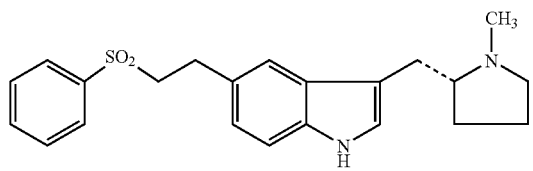

and is disclosed in WO-A-92/06973. Eletriptan is classified as a 5-$HT_{1B/1D}$ receptor agonist and is particularly useful for the treatment of migraine and for the prevention of migraine recurrence.

Anhydrous alpha- and beta-hydrobromide salt forms of eletriptan are disclosed in WO-A-96/06842.

WO-A-99/01135 (PCT/EP98/04176) discloses a pharmaceutical formulation including eletriptan hemisulphate and caffeine.

As previously mentioned, WO-A-96/06842 describes the anhydrous polymorphic alpha- and beta-hydrobromide salt forms of eletriptan. The problem addressed by the invention disclosed therein is to obtain a salt form of eletriptan that is, inter alia, stable and essentially non-hygroscopic in nature. That problem is solved by the provision of a stable, anhydrous, alpha-form of eletriptan hydrobromide. The anhydrous beta-form of eletriptan hydrobromide that is also described therein is stated not to be a viable option for the development of a suitable solid dosage form of the drug because it is unstable and has a tendency to undergo polymorphic conversion to the alpha-form previously described on attempted further processing.

The problem addressed by the present invention is to provide a further stable, non-hygroscopic, crystalline form of eletriptan hydrobromide which has acceptable solubility and dissolution characteristics, and which can be economically prepared and processed to provide suitable solid dosage forms of the drug.

Figure 1:
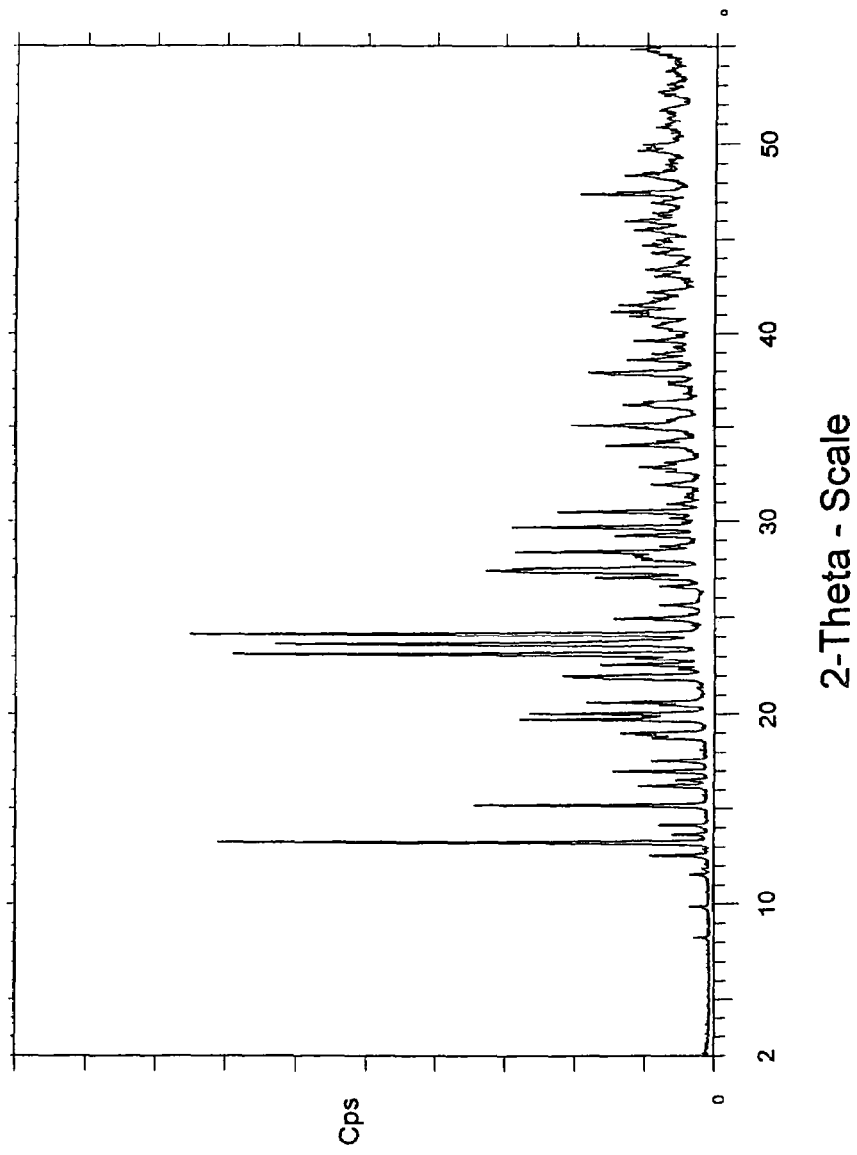
FIG. 1 shows the powder x-ray diffraction (PXRD) pattern of Form I of eletriptan hydrobromide monohydrate.

This problem has surprisingly been solved by the present invention that provides, in one aspect, eletriptan hydrobromide monohydrate. Eletriptan hydrobromide monohydrate has the formula (I):

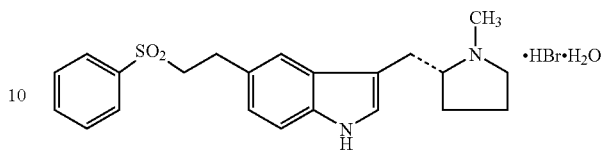

Eletriptan hydrobromide monohydrate is, most advantageously, stable under normal conditions and essentially non-hygroscopic. Also included within the scope of the present invention are radiolabelled derivatives and any other isotopic variations of eletriptan hydrobromide monohydrate.

It should be noted that WO-A-96/06842 does not disclose the preparation of eletriptan hydrobromide monohydrate. The anhydrous alpha-form of eletriptan hydrobromide mentioned therein is essentially non-hygroscopic under normal conditions as is demonstrated by the described hygroscopicity test results. These results show that it absorbs a maximum of 1.23% by weight of water on standing for 4 weeks at 40° C. and 90% relative humidity, that is under extreme conditions (an absorption of 3.9% by weight of water by anhydrous eletriptan hydrobromide would be required to form eletriptan hydrobromide monohydrate in this experiment). In contrast, the anhydrous beta-form of eletriptan hydrobromide mentioned therein is stated to be unstable and to undergo polymorphic conversion to the alpha-form on further processing. WO-A-96/06842 therefore does not specifically disclose a stable monohydrate form of eletriptan hydrobromide.

Eletriptan hydrobromide monohydrate has been made available by the surprising finding that treatment of a solution of eletriptan in water, or in a suitable organic solvent containing a sufficient amount of water to facilitate formation of the required monohydrate, with hydrogen bromide or a suitable source thereof, e.g. ammonium bromide, produces said monohydrate. In a second aspect the present invention therefore provides a process for the preparation of eletriptan hydrobromide monohydrate from eletriptan. Preferred organic solvents for use in this process include water-miscible or -immiscible organic solvents such as tetrahydrofuran (THF), acetone, methyl ethyl ketone, 1,2-dimethoxyethane, methyl isobutyl ketone, ethyl acetate and a $C_1$–$C_4$ alkanol (e.g. isopropanol). Most preferred organic solvents are THF and acetone. The solution of eletriptan may be treated with hydrogen bromide either in gaseous form or in the form of a suitable solution, e.g. dissolved in water, acetic acid, acetone or THF. Preferably, a concentrated (e.g. 48% or 62% by weight) solution of hydrogen bromide in water is used. Where non-aqueous sources of hydrogen bromide are used, water must be present in the reaction mixture. Alternatively, ammonium bromide may be used as a source of hydrogen bromide which forms a solution in the presence of water.

In a third aspect of the present invention it has been surprisingly found that any form of eletriptan hydrobromide other than the monohydrate, including mixtures thereof, may be converted to eletriptan hydrobromide monohydrate by crystallisation from water, or from a suitable organic solvent containing a sufficient amount of water to facilitate formation of the required monohydrate. Suitable organic solvents include acetone, THF, 1,2-dimethoxyethane and a $C_1$–$C_4$ alkanol, e.g. methanol.

In a fourth aspect of the present invention it has been found that any hydrated form of eletriptan hydrobromide, including eletriptan hydrobromide monohydrate, or mixtures thereof, may be converted to anhydrous eletriptan hydrobromide under suitable dehydration conditions. Suitable conditions include reslurry in, or crystallisation from, a suitable organic solvent, optionally with heating. Small amounts of water are tolerated in the organic solvent used in this process. Such dehydration conditions may optionally involve distillation or azeotropic distillation of the organic solvent used to remove the water associated with the hydrate. Preferred organic solvents for use in this process include toluene, acetone, THF and acetonitrile. Other suitable organic solvents include ethanol, n-propanol, isopropanol, t-butanol, industrial methylated spirit, methyl ethyl ketone, methyl isobutyl ketone, ethyl acetate, n-butyl acetate, cyclohexane, t-amyl alcohol, xylene and dichloromethane. Alternatively, this conversion may be effected by drying the hydrate, e.g. eletriptan hydrobromide monohydrate, either under reduced pressure and/or at elevated temperatures, or in a low-humidity environment.

Eletriptan hydrobromide monohydrate may be used for the treatment of a disease or condition for which a selective agonist of 5-HT$_1$ receptors, and particularly of 5-HT$_{1B/1D}$ receptors, is indicated. Such conditions include migraine, recurrent migraine, hypertension, depression, emesis, anxiety, an eating disorder, obesity, drug abuse, cluster headache, pain, chronic paroxysmal hemicrania and headache associated with a vascular disorder.

Eletriptan hydrobromide monohydrate can be administered alone but it will generally be administered in admixture with a suitable pharmaceutical excipient, diluent or carrier selected with regard to the intended route of administration and standard pharmaceutical practice.

For example, eletriptan hydrobromide monohydrate can be administered orally or sublingually in the form of tablets, capsules, ovules, elixirs, solutions or suspensions, which may contain flavouring or colouring agents, which may be formulated as immediate- or controlled-release, or fast-dissolving, compositions.

Such tablets may contain excipients such as microcrystalline cellulose, lactose, sodium citrate, calcium carbonate, dicalcium phosphate and glycine, disintegrants such as starch, croscarmellose sodium and certain complex silicates, and granulation binders such as polyvinylpyrrolidone, sucrose, gelatin and acacia. Additionally, lubricating agents such as magnesium stearate, glyceryl benhenate and talc may be included.

Solid compositions of a similar type may also be employed as fillers in gelatin capsules. Preferred excipients in this regard include lactose or milk sugar as well as high molecular weight polyethylene glycols. For aqueous suspensions and/or elixirs, eletriptan hydrobromide monohydrate may be combined with various sweetening or flavouring agents, colouring matter or dyes, with emulsifying and/or suspending agents and with diluents such as water, ethanol, propylene glycol and glycerin, and combinations thereof.

Eletriptan hydrobromide monohydrate can also be injected parenterally, for example, intravenously, intraperitoneally, intrathecally, intraventricularly, intrasternally, intracranially, intramuscularly or subcutaneously, or it may be administered by infusion techniques. It is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of eletriptan hydrobromide monohydrate will usually be from 0.1 to 4 mg/kg (in single or divided doses).

Thus tablets or capsules of eletriptan hydrobromide monohydrate may contain from 5 to 240 mg, preferably from 5 to 100 mg, of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Eletriptan hydrobromide monohydrate can also be administered intranasally or by inhalation and is conveniently delivered in the form of a dry powder inhaler or an aerosol spray presentation from a pressurised container or a nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of eletriptan hydrobromide monohydrate and a suitable powder base such as lactose or starch. Alternatively, eletriptan hydrobromide monohydrate may be administered intranasally by delivery from a non-pressurised unit or multi-dose, pump-type device.

Alternatively, eletriptan hydrobromide monohydrate can be administered in the form of a suppository or pessary, or it may be applied topically in the form of a lotion, solution, cream, ointment or dusting powder. Eletriptan hydrobromide monohydrate may also be transdermally administered by the use of a skin patch.

For application topically to the skin, eletriptan hydrobromide monohydratp can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Suitable formulations of eletriptan hydrobromide monohydrate are similar to those disclosed in WO-A-92/06973, WO-A-96/06842 and WO-A-99/01135. Preferred formulations of eletriptan hydrobromide monohydrate, particularly for use in the prevention of migraine recurrence, include dual-, sustained-, controlled-, delayed- or pulsed-release formulations.

Sustained-release dosage forms are designed to release eletriptan hydrobromide monohydrate to the gastro-intestinal tract of a patient over a sustained period of time following administration of the dosage form to the patient. Suitable dosage forms include:

(a) those in which eletriptan hydrobromide monohydrate is embedded in a matrix from which it is released by diffusion or erosion,
(b) those in which eletriptan hydrobromide monohydrate is present in or on a multiparticulate core which is coated with a rate controlling membrane,
(c) those in which eletriptan hydrobromide monohydrate is present in a dosage form containing a coating impermeable to the drug where release is via a drilled aperture, and
(d) those in which eletriptan hydrobromide monohydrate is released through a semi-permeable membrane, allowing the drug to diffuse across the membrane or through liquid filled pores within the membrane.

The skilled person would appreciate that some of the above means of achieving sustained-release may be combined, for example, a matrix containing the active compound may be formed into a multiparticulate and/or coated with an impermeable coating provided with an aperture.

Pulsed-release formulations are designed to release the active compound in pulses over a sustained period of time following administration of the dosage form to the patient. The release may then be in the form of immediate- or sustained-release. Delay in release may be achieved by releasing the drug at particular points in the gastrointestinal tract or by releasing drug after a pre-determined time. Pulsed-release formulations may be in the form of tablets or multiparticulates or a combination of both. Suitable dosage forms include:

(a) osmotic potential triggered release forms (e.g. see U.S. Pat. No. 3,952,741),
(b) compression coated two layer tablets (e.g. see U.S. Pat. No. 5,464,633),
(c) capsules containing an erodible plug (e.g. see U.S. Pat. No. 5,474,784),
(d) sigmoidal releasing pellets (e.g. as referred to in U.S. Pat. No. 5,112,621) and
(e) formulations coated with or containing pH dependent polymers including shellac, phthalate derivatives, polyacrylic acid derivatives and crotonic acid copolymers.

Dual-release formulations can combine the active compound in immediate-release form with additional active compound in sustained-release form. For example, a bilayer tablet can be formed with one layer containing eletriptan hydrobromide monohydrate in an immediate-release form and the other layer containing eletriptan hydrobromide monohydrate embedded in a matrix from which it is released by diffusion or erosion. Dual-release formulations can also combine the active compound in immediate-release form with additional active compound in pulsed-release form. For example, a capsule containing an erodible plug could liberate active compound initially and after a predetermined period of time further active compound may be delivered in immediate- or sustained-release form.

Preferred drug dual release profiles include
(a) immediate release followed by controlled release;
(b) immediate release followed by zero order release;
(c) immediate release followed by sigmoidal release; and
(d) double pulse release.

Delayed-release formulations are designed to release the active compound a predetermined time after administration. The release from delayed-release formulations may be in the form of immediate-release or sustained-release.

Controlled-release formulations impart control with respect to the rate of release or the time of release, or both, of the active compound and include sustained-, pulsed-, dual- and delayed-release formulations.

It is to be appreciated that all references herein to treatment include curative, palliative and prophylactic treatment.

The invention is illustrated by the following Examples.

EXAMPLE 1

Preparation of Eletriptan Hydrobromide Monohydrate from Eletriptan

Eletriptan (2 kg) was dissolved in acetone (24.2 L) and filtered. The mixture was diluted with further acetone (7.4 L) and water (2.36 L) added. A chilled (<5° C.) mixture of a solution of 48% by weight hydrogen bromide in water (0.863 kg) and acetone (12.4 L) was added in portions over about a 6 hour period whilst maintaining the temperature below 25° C. throughout the addition. Full transfer of the hydrogen bromide solution was ensured by washing the residues into the reaction mixture using further acetone (2.4 L). The resulting slurry was granulated and chilled prior to collection of the product obtained by filtration. The product was washed carefully with acetone and then dried under reduced pressure and at ambient temperature in the presence of a water reservoir to provide eletriptan hydrobromide monohydrate (1.75 kg, 70%). This material was then milled before further use.

$^1$H-NMR (400 MHz, $d_6$-DMSO): delta=10.90 (1H, d, J=2.2 Hz), 9.35 (1H, br s), 7.95 (2H, d, J=7.5 Hz), 7.76 (1H, t, J=7.5 Hz), 7.66 (2H, t, J=7.5 Hz), 7.38 (1H,s) 7.24 (1H, d, J=8.3 Hz), 7.23 (1H, d, J=2.2 Hz), 6.92 (1H, dd, J=8.3, 1.4 Hz), 3.63 (2H, m), 3.58 (2H, br m), 3.24 (1H, m), 3.06 (1H, m), 2.95 (2H, m), 2.86 (1H, m), 2.83 (3H, s), 2.00 (1H, m), 1.90 (2H, m), 1.70 (1H, m).

Found: C, 54.85; H, 6.03; N, 5.76. $C_{22}H_{29}N_2O_3SBr$ requires C, 54.87; H, 6.08; N, 5.82%.

PXRD, DSC, moisture sorption and IR data are provided in the Analytical Section that follows.

EXAMPLE 2

Preparation of Eletriptan Hydrobromide Monohydrate from Eletriptan

Eletriptan (1.9 kg) was dissolved in a solution of 97.5:2.5, by volume, THF:water (30 L) and filtered. A solution of hydrogen bromide (ca. 48% by weight) in water (0.87 kg) was added to the solution at 15–25° C. A dense crystalline slurry was formed. The slurry was heated under reflux for approximately one hour. The slurry was cooled to from 15 to 20° C. and granulated for a minimum of 1 hour. The product was filtered and washed with THF (10 L) to provide eletriptan hydrobromide monohydrate (2.3 kg).

Analytical data obtained were identical to those obtained for the product of Example 1.

EXAMPLE 3

Preparation of Eletriptan Hydrobromide Monohydrate from Eletriptan

Eletriptan (25 g) was dissolved in a solution of 95:5, by volume, THF:water and filtered. A solution of hydrogen bromide (ca. 48% by weight) in water (10.7 g) was added to the solution at 15–25° C. A dense crystalline slurry was formed. The slurry was heated under reflux for approximately one hour. The slurry was cooled to from 15 to 25° C. The product was filtered and washed with THF (50 ml) to produce eletriptan hydrobromide monohydrate (28.4 g, 96%).

Analytical data obtained were identical to those obtained for the product of Example 1.

EXAMPLE 4

Preparation of Eletriptan Hydrobromide Monohydrate by Reprocessing Eletriptan Hydrobromide Eletriptan hydrobromide (4.91 g) was dissolved in a mixture of acetone (10 ml) and water (1.85 ml) by heating under reflux. The mixture was treated with acetone (63.6 ml), dropwise over about 20 minutes, and then cooled to ambient temperature. The mixture was granulated overnight (16 hours), cooled to 0–5° C. and granulated at this temperature for a further hour. The resulting solid was filtered, washed with acetone (3 ml) and then dried under reduced pressure and at ambient temperature to give eletriptan hydrobromide monohydrate (4.8 g).

Analytical data obtained were identical to those obtained for the product of Example 1.

EXAMPLE 5

Preparation of Anhydrous Eletriptan Hydrobromide from Eletriptan Hydrobromide Monohydrate A slurry of eletriptan hydrobromide monohydrate (6.5 g) in acetone (97.5 ml) was heated under reflux for three hours and then cooled and filtered. The filtered solid was washed with acetone (6.5 ml) and dried under reduced pressure to give anhydrous eletriptan hydrobromide (5.78 g).

Figure 6:
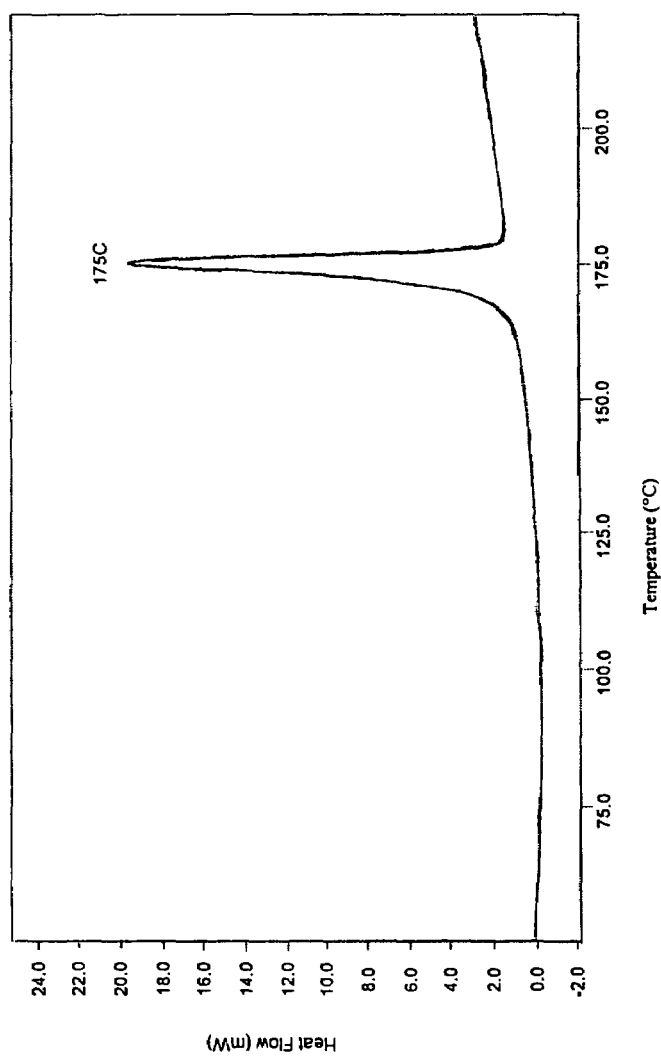
FIG. 6 shows the DSC thermogram obtained for the product of Example 5.

FIG. 6 shows the DSC thermogram obtained for this product by the method of paragraph (b) of the Analytical section below. This was consistent with that previously obtained for the alpha-form of anhydrous eletriptan hydrobromide described in WO-A-96/06842.

EXAMPLE 6

Preparation of Anhydrous Eletriptan Hydrobromide from Eletriptan Hydrobromide Monohydrate A slurry of eletriptan hydrobromide monohydrate (1.0 g) in toluene (30 ml) was heated under reflux. An aliquot of the toluene (5 ml) was removed by distillation and the mixture was held at below the reflux temperature for 2–3 hours. A further aliquot of toluene (5 ml) was removed by distillation. The residual slurry was cooled to ambient temperature over about one hour and the solid obtained collected by filtration and dried under reduced pressure at 60° C. to provide anhydrous eletriptan hydrobromide (0.81 g).

Figure 7:
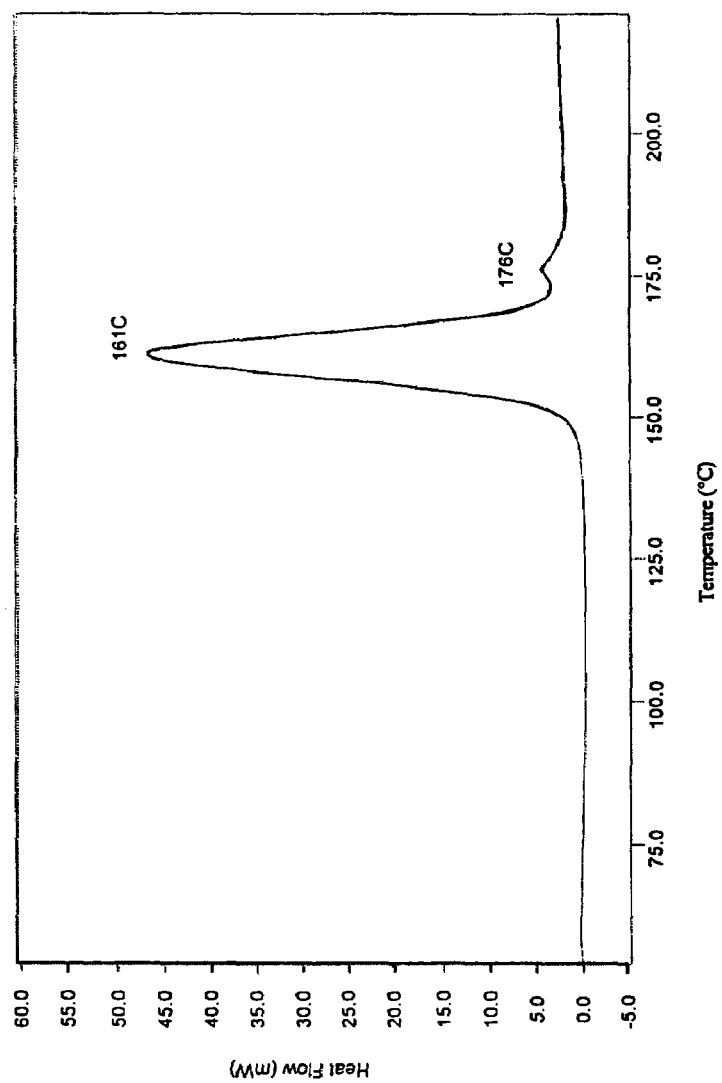
FIG. 7 shows the DSC thermogram obtained for the product of Example 6.

FIG. 7 shows the DSC thermogram obtained for this product by a similar method to that of paragraph (b) of the Analytical section below except that a 10 mg weight of sample and a heating rate of 40° C./minute were used. This showed the product to be a mixture of the alpha- and beta-forms of anhydrous eletriptan hydrobromide, both as disclosed in WO-A-96/06842, the former with an endotherm maximum at 176° C. and the latter with an endotherm maximum at 161° C. No evidence for the presence of eletriptan hydrobromide monohydrate was detected in this DSC analysis.

EXAMPLE 7

Preparation of a Tablet Formulation of Eletriptan Hydrobromide Monohydrate

Each Tablet to Contain:

| | |
|---|---|
| Eletriptan hydrobromide monohydrate | 100.629 mg |
| Microcrystalline cellulose (Avicel PH102, trade mark) | 182.371 mg |
| Lactose (fast-flo) | 92.000 mg |
| Croscarmellose sodium (Ac-di-sol) | 20.000 mg |
| Magnesium stearate | 3.000 mg |
| Magnesium stearate | 2.000 mg |
| Total | 400.000 mg |

Eletriptan hydrobromide monohydrate was blended with lactose for 10 minutes and then microcrystalline cellulose and croscarmellose sodium added. The mixture was blended for 20 minutes and screened through a 500 micron screen. The screened material was blended for a further 20 minutes and a first portion of magnesium stearate (0.75% w/w) added. The mixture was roller compacted and blended for 20 minutes then a second portion of magnesium stearate (0.50% w/w) added. The mixture was compressed into tablets each containing a 80 mg dose of eletriptan. The tablets were then film-coated using Opadry Orange (trade mark) film coat (OY-LS-23016) as a 12% solids system at 3.0% w/w followed by Opadry Clear (trade mark) overcoat (YS-2-19114-A) as a 5% solution at 0.5% w/w.

Analytical Data

Analytical data obtained for eletriptan hydrobromide monohydrate prepared by the method of Example 1 are presented below.

a) PXRD

The powder X-ray diffraction (PXRD) pattern was determined using a Siemens D5000 powder X-ray diffractometer fitted with an automatic sample changer, a theta-theta goniometer, automatic beam divergence slits, a secondary monochromator and a scintillation counter.

The sample was prepared for analysis by packing the powder sample into a 12 mm diameter, 0.25 mm deep cavity that had been cut into a silicon wafer specimen mount. The specimen was rotated whilst being irradiated with copper K-alpha, X-rays (wavelength=1.5046 Angstroms) with the X-ray tube operated at 40 kV/40 mA. The analysis was performed with the goniometer running in step-scan mode set for a 5 second count per 0.02° step over a two-theta range of 2° to 55°.

Table 1 shows the peak listings for FIG. 1 in which dA° is a measurement of the interplanar spacing and $I/I_i$ is a measurement of the relative intensity.

TABLE 1

| dÅ | $I/I_i$ |
|---|---|
| 10.76 | 3.6 |
| 9.015 | 4.6 |
| 7.697 | 4.4 |
| 7.496 | 1.8 |
| 7.084 | 12.0 |
| 6.700 | 94.4 |
| 6.507 | 7.8 |
| 6.288 | 10.1 |

TABLE 1-continued

| dÅ | I/I$_i$ |
|---|---|
| 5.849 | 45.4 |
| 5.475 | 14.3 |
| 5.377 | 7.3 |
| 5.227 | 19.2 |
| 5.093 | 4.4 |
| 5.060 | 10.7 |
| 4.735 | 12.0 |
| 4.716 | 9.3 |
| 4.697 | 15.3 |
| 4.680 | 17.0 |
| 4.502 | 36.9 |
| 4.475 | 14.8 |
| 4.435 | 35.1 |
| 4.337 | 11.8 |
| 4.305 | 24.1 |
| 4.164 | 4.7 |
| 4.060 | 28.8 |
| 4.048 | 27.0 |
| 3.979 | 6.7 |
| 3.941 | 21.6 |
| 3.890 | 15.0 |
| 3.847 | 91.8 |
| 3.764 | 84.0 |
| 3.738 | 25.4 |
| 3.684 | 100.0 |
| 3.569 | 19.1 |
| 3.474 | 10.3 |
| 3.351 | 10.2 |
| 3.295 | 22.6 |
| 3.264 | 40.3 |
| 3.253 | 43.5 |
| 3.241 | 40.3 |
| 3.189 | 15.7 |
| 3.178 | 15.0 |
| 3.165 | 17.0 |
| 3.143 | 37.7 |
| 3.110 | 10.2 |
| 3.048 | 16.6 |
| 3.040 | 11.5 |
| 3.006 | 38.4 |
| 2.959 | 8.5 |
| 2.925 | 29.8 |
| 2.889 | 8.9 |
| 2.857 | 8.1 |
| 2.797 | 11.9 |
| 2.739 | 9.2 |
| 2.719 | 14.3 |
| 2.699 | 9.3 |
| 2.629 | 20.5 |
| 2.612 | 10.8 |
| 2.564 | 17.3 |
| 2.554 | 27.0 |
| 2.532 | 8.9 |
| 2.480 | 17.3 |
| 2.468 | 15.2 |
| 2.407 | 8.5 |
| 2.401 | 10.5 |
| 2.370 | 23.9 |
| 2.328 | 16.7 |
| 2.324 | 13.1 |
| 2.310 | 11.9 |
| 2.305 | 10.7 |
| 2.290 | 7.7 |
| 2.271 | 15.2 |
| 2.265 | 12.0 |
| 2.229 | 11.8 |
| 2.201 | 16.2 |
| 2.190 | 19.7 |
| 2.171 | 17.5 |
| 2.152 | 14.4 |
| 2.138 | 12.6 |
| 2.096 | 10.5 |
| 2.081 | 13.4 |
| 2.066 | 7.3 |
| 2.041 | 12.1 |
| 2.024 | 13.8 |
| 2.010 | 11.1 |

TABLE 1-continued

| dÅ | I/I$_i$ |
|---|---|
| 2.005 | 11.5 |
| 1.988 | 15.4 |
| 1.968 | 15.9 |
| 1.958 | 13.1 |
| 1.951 | 11.9 |
| 1.929 | 11.4 |
| 1.913 | 25.6 |
| 1.908 | 21.2 |
| 1.877 | 17.2 |
| 1.872 | 14.9 |
| 1.832 | 14.8 |
| 1.827 | 14.9 |
| 1.823 | 13.3 |
| 1.792 | 11.1 |
| 1.776 | 9.3 |
| 1.762 | 10.4 |
| 1.740 | 9.8 |
| 1.734 | 10.9 |
| 1.721 | 9.3 |
| 1.701 | 9.6 | b) DSC

Differential scanning calorimetry (DSC) was performed using a Perkin-Elmer DSC-7 instrument fitted with an automatic sample changer. Approximately 3 mg of sample was accurately weighed into a 50 microlitre aluminium pan and crimp-sealed with a perforated lid. The sample was heated at 20° C./minute over the range 40 to 220° C. with a nitrogen gas purge.

Figure 2:
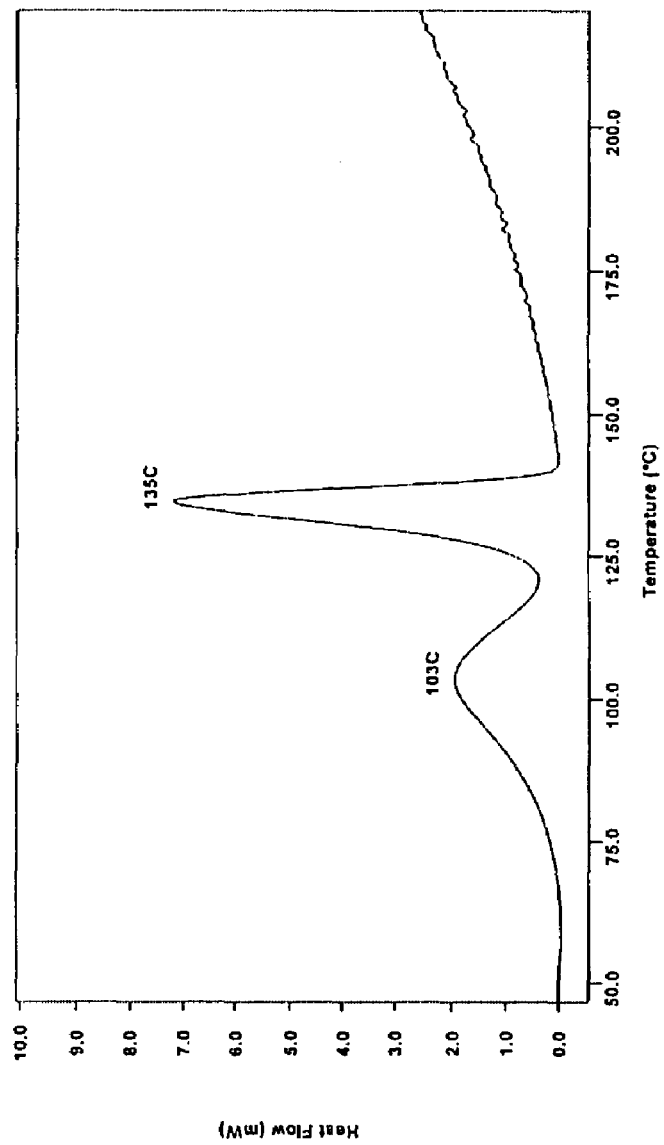
FIG. 2 shows the differential scanning calorimetry (DSC) thermogram of eletriptan hydrobromide monohydrate.

FIG. 2 shows the DSC thermogram obtained.

The DSC thermogram of FIG. 2 shows a broad endotherm at 103° C. due to the dehydration of the monohydrate followed by a melting endotherm at 135° C.

c) Moisture Sorption

The moisture sorption of eletriptan hydrobromide monohydrate was determined using a Dynamic Vapour Sorption (DVS) Automated Sorption Analyser Model DVS-1 instrument manufactured by Surface Measurements Systems Ltd., UK.

Approximately 25 mg of eletriptan hydrobromide monohydrate was accurately weighed into a sample pan. This was exposed to humidities in the range of from 0 to 90% RH. The analysis was carried out in detail in the range of from 0 to 15% RH, using 15% RH steps in the range of from 15 to 90% RH. The analysis temperature was 30° C. with a nitrogen flow rate of 200 cm$^3$min$^{-1}$.

Figure 3:
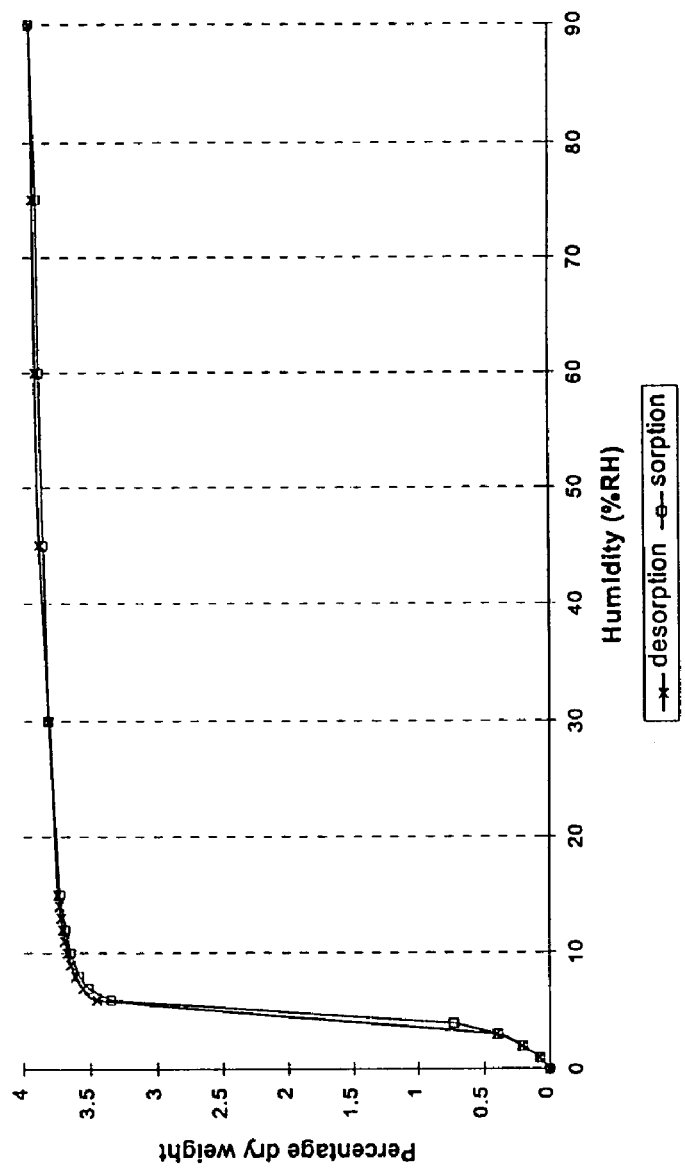
FIG. 3 shows the moisture sorption isotherm obtained for eletriptan hydrobromide monohydrate.

FIG. 3 shows the moisture sorption isotherm obtained for eletriptan hydrobromide monohydrate. This isotherm shows that above 6% RH the sample remains as a monohydrate but at 0% RH the material has lost all of the 3.8% w/w of water associated with its monohydrate molecular structure. Once the monohydrate has formed there is very little additional moisture sorbed and within the range 10 to 90% RH less than 0.3% w/w of water is sorbed. These data illustrate that eletriptan hydrobromide monohydrate is essentially non-hygroscopic.

d) IR

Infrared (IR) spectroscopy was performed with a Nicolet 800 FT-IR spectrometer fitted with a d-TGS detector. The spectrum was acquired at 2 cm$^{-1}$ resolution from a KBr disc preparation of the sample.

Figure 4:
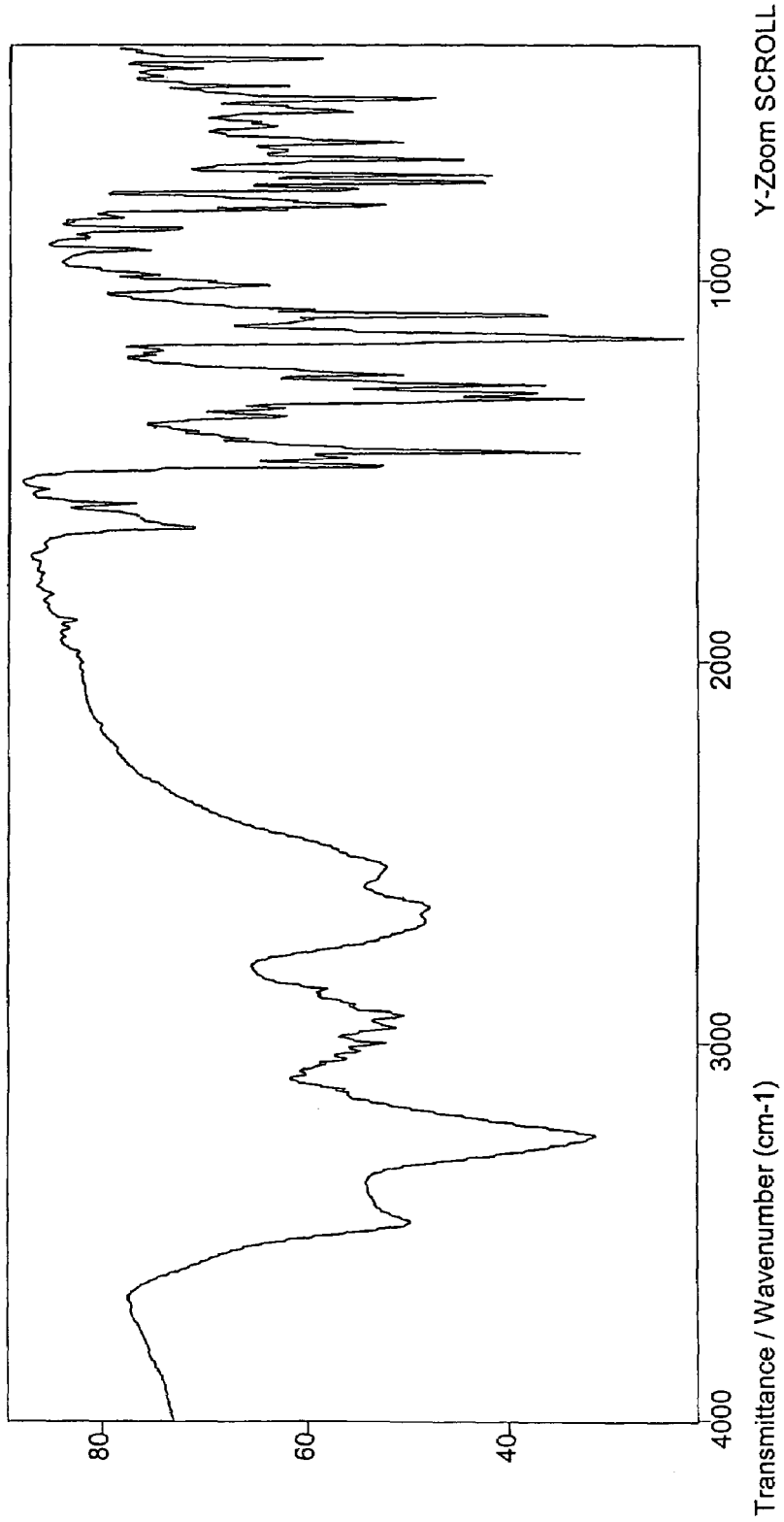
FIG. 4 shows the infra red (IR) spectrum of eletriptan hydrobromide monohydrate (4000–400 $cm^{-1}$)
Figure 5:
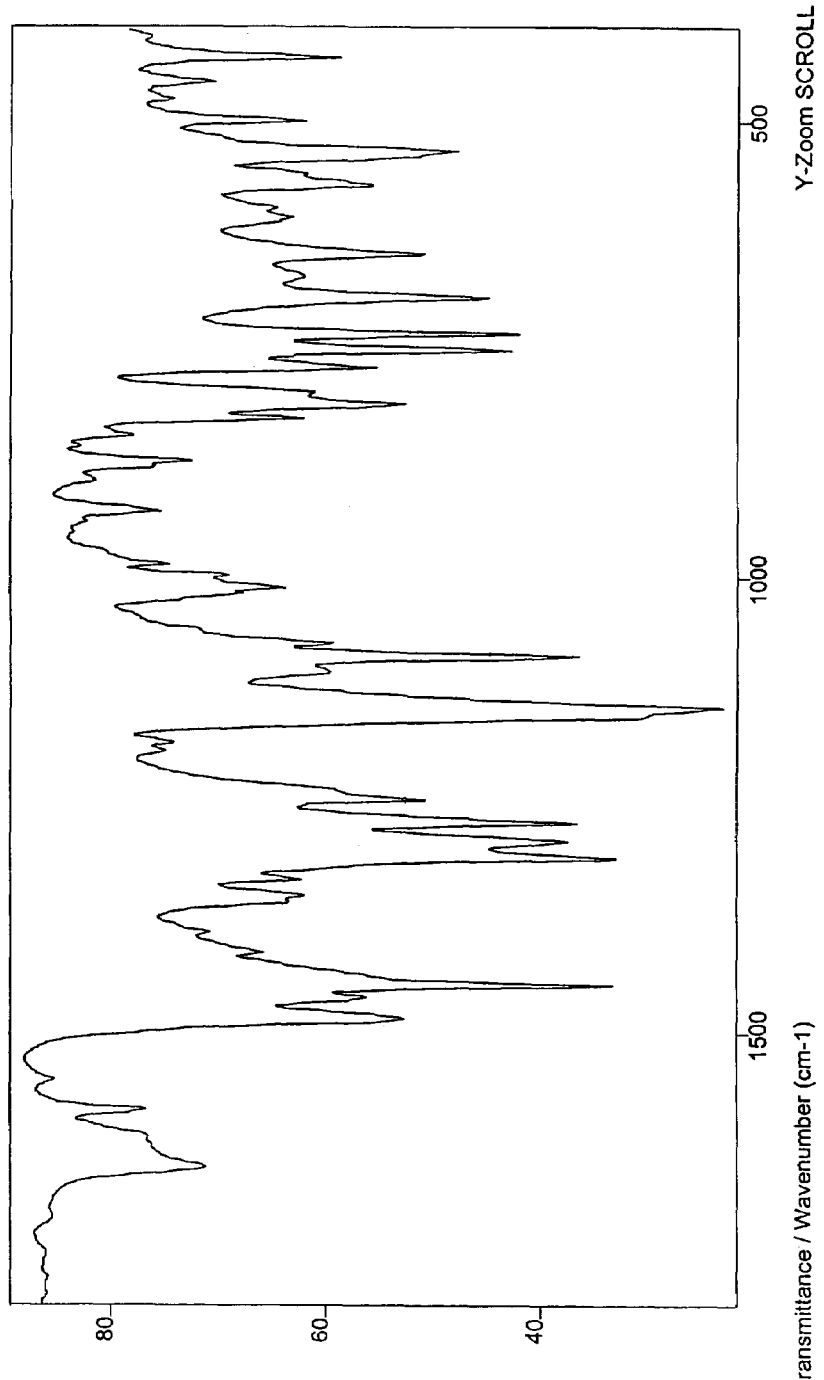
FIG. 5 shows the IR spectrum of eletriptan hydrobromide monohydrate (1800–400 $cm^{-1}$)

FIGS. 4 and 5 show the IR spectra obtained.

Table 2 gives the peak listing for FIGS. 4 and 5 in which the wavenumber (cm$^{-1}$) of each peak is recorded.

TABLE 2

Peak position and intensity data from FIGS. 4 and 5

| cm$^{-1}$ | % T |
|---|---|
| 406.9 | 76.26 |
| 429.6 | 58.71 |
| 456.6 | 70.18 |
| 473.9 | 74.14 |
| 497.1 | 61.84 |
| 529.2 | 47.58 |
| 553.9 | 61.60 |
| 566.4 | 55.54 |
| 592.2 | 64.48 |
| 601.1 | 62.96 |
| 606.2 | 64.21 |
| 642.2 | 50.81 |
| 665.0 | 62.00 |
| 667.3 | 61.99 |
| 689.1 | 44.63 |
| 729.5 | 41.77 |
| 747.8 | 42.52 |
| 767.2 | 55.12 |
| 793.0 | 61.03 |
| 807.2 | 52.47 |
| 822.0 | 61.96 |
| 841.2 | 77.97 |
| 852.8 | 82.78 |
| 870.1 | 72.30 |
| 876.3 | 75.82 |
| 890.9 | 81.30 |
| 926.3 | 75.29 |
| 937.9 | 82.07 |
| 948.9 | 83.39 |
| 970.5 | 80.26 |
| 985.0 | 74.49 |
| 997.3 | 68.84 |
| 1010.2 | 63.67 |
| 1017.4 | 67.60 |
| 1071.0 | 59.34 |
| 1085.7 | 36.28 |
| 1102.4 | 59.40 |
| 1141.0 | 22.80 |
| 1150.4 | 29.87 |
| 1178.5 | 74.00 |
| 1189.1 | 74.80 |
| 1241.0 | 50.56 |
| 1267.1 | 36.51 |
| 1287.8 | 37.31 |
| 1305.4 | 32.74 |
| 1328.5 | 62.22 |
| 1346.7 | 62.04 |
| 1353.4 | 63.40 |
| 1387.3 | 70.61 |
| 1408.8 | 65.76 |
| 1444.9 | 33.08 |
| 1458.1 | 56.13 |
| 1482.5 | 52.58 |
| 1549.0 | 85.24 |
| 1581.3 | 76.69 |
| 1611.6 | 76.36 |
| 1622.0 | 76.12 |
| 1646.6 | 70.94 |
| 1703.4 | 85.34 |
| 1827.7 | 84.61 |
| 1893.3 | 82.46 |
| 1913.9 | 83.22 |
| 1937.2 | 83.53 |
| 1978.6 | 82.08 |
| 2001.7 | 81.75 |
| 2676.9 | 48.34 |
| 2852.6 | 58.00 |
| 2864.6 | 58.53 |
| 2893.3 | 55.24 |
| 2921.6 | 50.36 |
| 2952.9 | 51.31 |
| 2971.5 | 54.94 |
| 2994.2 | 52.24 |
| 3013.8 | 54.84 |
| 3038.5 | 56.17 |

TABLE 2-continued

Peak position and intensity data from FIGS. 4 and 5

| cm$^{-1}$ | % T |
|---|---|
| 3054.5 | 58.05 |
| 3071.0 | 60.25 |
| 3079.6 | 60.08 |
| 3117.0 | 56.27 |
| 3131.2 | 55.95 |
| 3246.0 | 31.56 |
| 3473.4 | 49.70 |

Stability Data

1) Eletriptan hydrobromide monohydrate was stored in double polyethylene bags inside a fibreboard drum under the following conditions:
25° C./60% RH for 9 months
30° C./60% RH for 9 months
40° C./75% RH for 6 months
(RH=relative humidity)
HPLC analysis of the products at the end of the storage periods showed no degradation had occurred.

2) A batch of the tablets prepared according to Example 7 was stored in HDPE (high density polyethylene) bottles under the following conditions:
25° C./60% RH for 9 months
30° C./60% RH for 9 months
40° C./175% RH for 6 months
(RH=relative humidity)
HPLC analysis of the tablets at the end of the storage periods showed no degradation had occurred.

The results of both stability tests show that eletriptan hydrobromide monohydrate exhibits good stability.

The invention claimed is:

1. Eletriptan hydrobromide monohydrate of the formula (I):

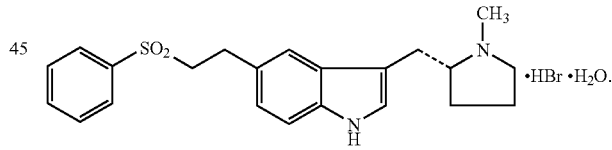

2. A pharmaceutical composition including eletriptan hydrobromide monohydrate as claimed in claim 1 together with a pharmaceutically acceptable excipient, diluent or carrier.

3. A method for treating a disease or condition selected from migraine and recurrent migraine in an mammal which includes administering to said mammal an effective amount of eletriptan hydrobromide monohydrate as claimed in claim 1.

4. A process for the preparation of eletriptan hydrobromide monohydrate as claimed in claim 1 which comprises treatment of a solution of eletriptan in water, or in an organic solvent containing at least 4% by volume of water based on the total volume of water and solvent to facilitate formation of the required monohydrate, with hydrogen bromide.

5. A process as claimed in claim 4 wherein the organic solvent is tetrahydrofuran or acetone.

6. A process as claimed in claim 4 wherein hydrogen bromide is used in the form of an aqueous solution.

7. A process for the preparation of eletriptan hydrobromide monohydrate as claimed in claim 1 which comprises crystallization of eletriptan hydrobromide, or a mixture thereof, from water, or from an organic solvent containing at least 4% by volume of water based on the total volume of water and solvent to facilitate formation of the required monohydrate.

8. A process as claimed in claim 7 wherein the organic solvent is acetone.

9. A process for the preparation of anhydrous eletriptan hydrobromide which comprises dehydration of any hydrated form of eletriptan hydrobromide including eletriptan hydrobromide monohydrate as claimed in claim 1, or a mixture thereof.

* * * * *